United States Patent [19]

Georgiev et al.

[11] Patent Number: 4,769,469

[45] Date of Patent: Sep. 6, 1988

[54] 5-(PHENYL OR PHENOXYALKYL)-3-(2-FURANYL)-3-(1H-IMIDAZOL-1-YLMETHYL)-2-METHYLISOXAZOLIDINES

[75] Inventors: Vassil S. Georgiev, Rochester; George B. Mullen, Avon, both of N.Y.

[73] Assignee: Pennwalt Corporation, Philadelphia, Pa.

[21] Appl. No.: 36,839

[22] Filed: Apr. 10, 1987

[51] Int. Cl.$^4$ .................... A01N 43/52; C07D 233/60
[52] U.S. Cl. .................... 548/240; 548/336; 549/483
[58] Field of Search .................... 548/240

[56] References Cited

U.S. PATENT DOCUMENTS

| | | | |
|---|---|---|---|
| 3,709,901 | 1/1973 | Draber et al. | 548/235 |
| 3,711,495 | 1/1973 | Kulsa et al. | 548/240 |
| 3,915,978 | 10/1975 | Kulsa et al. | 548/240 |
| 3,987,179 | 10/1975 | Nadelson | 514/378 |
| 4,010,176 | 3/1977 | Kulsa et al. | 548/242 |
| 4,510,154 | 4/1985 | Yoshida et al. | 514/365 |
| 4,719,306 | 1/1988 | Georgiev | 548/240 |
| 4,723,021 | 2/1988 | Georgiev | 548/240 |

FOREIGN PATENT DOCUMENTS

| | | | |
|---|---|---|---|
| 171137 | 2/1986 | European Pat. Off. | 548/215 |
| 54-76579 | 6/1979 | Japan . | |
| 1288213 | 9/1972 | United Kingdom | 548/240 |

OTHER PUBLICATIONS

Sokolov, S. V. et al., Chemical Abstract 55:7399 (1961), Abstracting "Isoxazole Compounds III, Synthesis of Some Isoxazolylazoles", Zhur. Obshchei Khim. 30, pp. 1781–1787 (1960).
Kano, H. et al., Chem. Abstract 62:9139A (1965), Abstracting French 1,376,432 (Oct. 23, 1964).
Kano, H. et al., Chem. Abstract 63:8367a (1965), Abstracting French 1,380,177 (Nov. 27, 1964).
Takahi, Y. et al., Chem. Abstract 81:22233c (1974), Abstracting Japan Kokai 7,399,336 (Dec. 15, 1973).
Boyce, C. B. et al., Chem. Abstract 87:23258a (1977), Abstracting German Offen. 2,639,189 (Mar. 10, 1977).
Funaki, Y. et al., Chem. Abstract 92:128915u (1980), Abstracting Japan Kokai 79, 76,579 (Jun. 19, 1979).
Kelly, R. C. et al., Chem. Abstract 93:114498u (1980), Abstracting German Offen. 2,918,878 (Nov. 22, 1979).
Haken, P. T. et al., Chem. Abstract 93:132471j (1980), Abstracting Brit. Pat. Appln. 2,024,218 (Jan. 9, 1980).

*Primary Examiner*—Donald G. Daus
*Assistant Examiner*—Mark W. Noel

[57] ABSTRACT

5-(phenyl or phenoxymethyl)-3-(2-furanyl)-3-(1H-imidazol-1-ylmethyl)-2-methylisoxazolidine and related derivatives in which one or more hydrogens on the phenyl ring are replaced by halogen, lower alkyl, lower alkoxy, nitro and combinations thereof are useful as antifungal agents.

5 Claims, No Drawings

5-(PHENYL OR PHENOXYALKYL)-3-(2-FURANYL)-3-(1H-IMIDAZOL-1-YLMETHYL)-2-METHYLISOX-AZOLIDINES

BACKGROUND OF THE INVENTION

This invention pertains generally to substituted 2-methylisoxazolidines and more specifically to 5-(phenyl or phenoxymethyl)-3-(2-furanyl)-3-(1H-imidazol-1-ylmethyl)-2-methylisoxazolidines which are useful as antifungal agents.

BRIEF SUMMARY OF THE INVENTION

In accordance with this invention there are provided compounds of the formula:

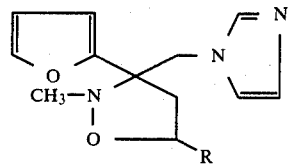

and the pharmaceutically acceptable acid addition salts thereof, in the form of their enantiomers or mixtures of their enantiomers including diastereoisomeric pairs of such enantiomers, wherein;

R is selected from phenyl, substituted phenyl, phenoxymethyl and substituted phenoxymethyl groups wherein the substituents on the substituted phenyl and phenoxymethyl groups are selected from halogen, nitro, lower alkyl, lower alkoxy and combinations thereof.

DETAILED DESCRIPTION OF THE INVENTION

The compounds of this invention are useful as antifungal agents. They have been shown to exert in vitro activity against yeast and systemic mycoses and dermatophytes as determined by broth and agar testing techniques [McGinnis, M. R., *Laboratory Handbook of Medical Mycology*, Academic Press, N.Y., N.Y. (1980)]. The compounds prepared in Examples 1 and 3 below were found to have good to moderate inhibitory activity against a broad spectrum of fungi including trichophyton mentagrophytes, trichophyton tonsurans, trichophyton schoenleinii, epidermophyton floccosum and candida albicans (minimum inhibitory concentration MIC, of <0.2 to 70 ug/ml).

Because of their antifungal activity, the compounds of the invention can be used, for example, in suitable liquid, semi-solid or solid carriers in the form of solutions, emulsions, suspensions, dispersions, ointments, aerosols, soaps, detergents, and powders in amounts effective to combat systemic and dermatophylic fungal infections in warm blooded animals (1 to 20 percent active ingredient).

The compounds of this invention are those of the formula:

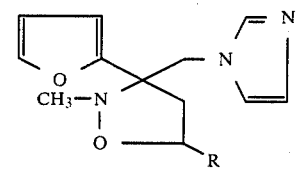

and the pharmaceutically acceptable acid addition salts thereof, in the form of their enantiomers or mixtures of their enantiomers including diastereoisomeric pairs of such enantiomers,
wherein;

R represents phenyl, substituted phenyl, phenoxymethyl or substituted phenoxymethyl groups. The substituents on the substituted phenyl rings are selected from halogen, nitro, lower alkyl, lower alkoxy and combinations thereof. By halogen is meant chlorine, bromine, fluorine and iodine, with chlorine and fluorine being preferred. By lower alkyl and lower alkoxy is meant groups having one to four (1-4) carbons which can be a branched or unbranched chain.

The 5-(phenyl or phenoxymethyl)-3-(2-furanyl)-3-(1H-imidazol-1-ylmethyl)-2-methylisoxazolidine derivatives are obtained as mixtures of cis- and trans-diastereomers due to the presence of two asymmetric carbon atoms in the isoxazolidine ring. The diastereomeric mixture is conveniently separated by flash-chromatography on silica gel using halogenated hydrocarbons (preferably dichloromethane and chloroform), alkanols (preferably methanol and ethanol), ethyl acetate and such, as eluents. The said eluents may be used alone or in combinations such as the ones comprised of 95-99% halogenated hydrocarbon and 1-5% alkanol by volume. The stereochemistry of the two asymmetric carbon atoms in the isoxazolidine ring may be determined by conventional methods that include x-ray crystallography, nuclear magnetic resonance spectroscopy, circular dichroism and optical rotatory dispersion. Both the cis and trans stereoisomers are resolvable into their optical enantiomers with (+) and (−) optical rotations by standard techniques such as fractional recrystallization of the diastereomeric salts with optically active organic acids such as (+) and (−)-tartaric acid, (+) and (−)-dibenzoyltartaric acid and the like.

As illustrated in the following diagram, the compounds of this invention can be prepared by an initial bromination of 2-acetylfuran 1, and reacting the resulting bromo derivatives with imidazole to produce the 1-(2-furanyl)-2-(1H-imidazol-1-yl)ethanone (3). Reaction of compound 3 with N-methylhydroxylamine hydrochloride provides the 1-(2-furanyl)-2-(1H-imidazol-1-yl)-N-methylethanimine N-oxide (4) which is included in the subject matter of our co-pending application Ser. No. 900,856 filed Aug. 27, 1986 entitled "α-Substituted Ketonitrone Derivatives" whose disclosure is incorporated herein by reference. The nitrone compound 4 is then treated with styrene or an appropriate styrene (or allyl phenyl ether) derivative 5 to give a diastereomeric mixture of the desired cis- and trans-5-(phenyl or phenyoxmethyl)-3-(2-furanyl)-3-(1H-imidazol-1-ylmethyl)-2-methylisoxazolidine 6.

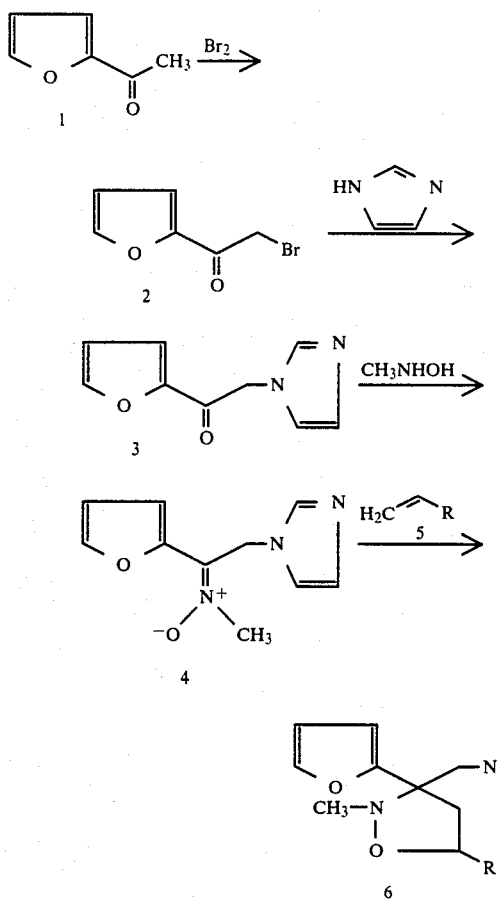

The compounds of this invention are basic and thus can form salts with pharmaceutically acceptable inorganic and organic acids such as, for example, acetic acid, maleic acid, malic acid, fumaric acid, succinic acid, succinamic acid, tartaric acid, citric acid, lactic acid, hydrochloric acid, hydrobromic acid, hydroiodic acid, nitric acid, sulfuric acid and phosphoric acid.

The preparation of the compounds of this invention is further illustrated by the following syntheses of intermediates and in the Examples.

Preparation of 2-Bromo-1-(2-furanyl)ethanone (2)

Bromine (71.14 ml, 1.39 mol) is added dropwise over 1 hour to a solution of 117.59 g (1.07 mol) of 2-acetylfuran (1) in a mixture of 900 ml of either and 400 ml of 1,4-dioxane, at 0° C. under a nitrogen atmosphere. The reaction is warmed to ambient temperature and stirred for 18 hours, then quenched with 1.1 liter of saturated aqueous ammonium chloride and extracted with chloroform. The organic layer is dried over anhydrous magnesium sulfate and concentrated in vacuo to give a dark oil. Flash-chromatography on neutral silica gel using chloroform as eluent followed by distillation using a Kugelruhr apparatus gives 190.81 g (94%) of compound 2 as a light yellow oil, boiling point 85° C. (0.30 mmHg).

Preparation of 1-(2-Furanyl)-2-(1H)-imidazol-1-yl)ethanone (3)

To a solution of 8.88 g (0.13 mol) of imidazole and 18.2 ml (0.13 mol) of triethylamine in 180 ml of methanol at 0° C. under a nitrogen atmosphere, a solution of 24.66 g (0.13 mol) of 2-bromo-1-(2-furanyl)ethanone (2) in 50 ml of 1,4-dioxane is added dropwise over 40 min. The reaction mixture is warmed gradually to ambient temperature and stirred for 16 hours, diluted with water and extracted with chloroform. The organic layer is dried over anhydrous magnesium sulfate, concentrated in vacuo, and flash-chromatographed on neutral silica gel using ethyl acetate as eluent to give 20.0 g (87%) of compound 3, melting point 91°–94° C. (ethyl acetate). Anal. Calcd. for $C_9H_8N_2O_2$: C, 61.36; H, 4.58; N, 15.90. Found: C, 61.40; H, 4.72; N, 15.83.

Preparation of 1-(2-Furanyl)-2-(1H-imidazol-1-yl)-N-methylethanimine N-oxide (4)

Under a nitrogen atmosphere, a mixture of 21.32 g (0.121 mol) of 1-(2-furanyl)-2-(1H-imidazol-1-yl)ethanone (3), 15.16 g (0.182 mol) of N-methylhydroxylamine hydrochloride, and 14.89 g (0.182 mol) of sodium acetate in 400 ml of ethanol is stirred at ambient temperature for 4 days. Sodium bicarbonate (30.58 g, 0.364 mol) is added and the mixture filtered. The filtrate is concentrated in vacuo and flash-chromatographed on neutral silica gel using a 98:2 by volume mixture of chloroform and methanol as eluent to give 8.30 g (33%) of compound 4, melting point 130°–133° C. (ethyl acetate). Anal. Calcd. for $C_{10}H_{11}N_3O_2$: C, 58.53; H, 5.40; N, 20.48. Found: C, 58.60; H, 5.47; N, 20.49.

EXAMPLE 1

5-(4-Chlorophenyl)-3-(2-furanyl)-3-(1H-imidazol-1-ylmethyl)-2-methylisoxazolidine (6, R=$C_6H_4Cl$—4)

A solution of 7.60 g (0.037 mol) of 1-(2-furanyl)-2-(1H-imidazol-1-yl)-N-methylethanimine N-oxide (4) and 7.70 g (0.056 mol) of 4-chlorostyrene in 400 ml of toluene is refluxed for 48 hours under a nitrogen atmosphere. Upon cooling to ambient temperature, the crude cis- and trans-diastereomeric mixture of compound 6 (R=$C_6H_4Cl$—4) is concentrated in vacuo and flash-chromatographed on neutral silica gel using a 98:2 by volume mixture of chloroform and methanol to give 1.30 g (10%) of isomer A, melting point 99°–101° C. (ethyl acetate-hexane, 1:1 by volume). Anal. Calcd. for $C_{18}H_{18}ClN_3O_2$: C, 62.88; H, 5.28; Cl, 10.31; N, 12.22 Found: C, 62.90; H, 5.39; Cl, 10.44; N, 12,13. Isomer B (1.10 g, 8.5%) has a melting point of 131°–133° C. (ethyl acetate-hexane, 1:1 by volume). Anal. Calcd. for $C_{18}H_{18}ClN_3O_2$: C, 62.88; H, 5.28; Cl, 10.31; N, 12.22. Found: C, 62.82; H, 5.28; Cl, 10.46; N, 12.12.

EXAMPLE 2

3-(2-Furanyl)-3-(1H-imidazol-1-ylmethyl)-2-methyl-5-(3-nitrophenyl)isoxazolidine (6, R=$C_6H_4NO_2$—3)

Compound 4 (R=$C_6H_4NO_2$—3) is prepared by a method similar to that described in Example 1 by reacting 1-(2-furanyl)-2-(1H-imidazol-1-yl)-N-methylethanimine N-oxide (4) with 3-nitrostyrene. The resulting cis- and trans-diastereomeric mixture of compound 6 (R=$C_6H_4NO_2$—3) is flash-chromatographed on neutral silica gel using a 98:2 by volume mixture of chloroform and methanol as eluent. Isomer A has melting point of 120°–123° C. (ethyl acetate-hexane, 1:1 by volume) Anal. Calcd. for $C_{18}H_{18}N_4O_4$: C, 61.01; H, 5.12; N, 15.81. Found: C, 60.96; H, 5.26; N, 15.88.

EXAMPLE 3

5-(4-Chlorophenoxymethyl)-3-(2-furanyl)-3-(1H-imidazol-1-ylmethyl)-2-methylisoxazolidine (6, R=CH$_2$OC$_6$H$_4$Cl—4)

Compound 4 (R=CH$_2$OC$_6$H$_4$Cl—4) is prepared by a method similar to that described in Example 1 by reacting 1-(2-furanyl)-2-(1H-imidazol-1-yl)-N-methylethanimine N-oxide (4) with allyl 4-chlorophenyl ether. The resulting cis- and trans-diastereomeric mixture of compound 6 (R=CH$_2$OC$_6$H$_4$Cl—4) is flash-chromatographed on neutral silica gel using a 98:2 by volume mixture of chloroform and methanol as eluent. Isomer A has melting point of 150°–152° C. (ethyl acetate). Anal. Calcd. for C$_{19}$H$_{20}$ClN$_3$O$_3$: C, 61.04; H, 5.39; Cl, 9.48; N, 11.24. Found: C, 60.99; H, 5.41; Cl, 9.52; N, 11.21.

EXAMPLE 4

3-(2-Furanyl)-3-(1H-imidazol-1-ylmethyl)-5-(4-methoxyphenoxymethyl)-2-methylisoxazolidine (6, R=CH$_2$OC$_6$H$_4$OCH$_3$—4)

Compound 4 (R=CH$_2$OC$_6$H$_4$OCH$_3$—4) is prepared by a method similar to that described in Example 1 by reacting 1-(2-furanyl)-2-(1H-imidazol-1-yl)-N-methylethanimine N-oxide (4) with allyl 4-methoxyphenyl ether. The resulting cis- and trans-diastereomeric mixture of compound 6 (R=CH$_2$OC$_6$H$_4$OCH$_3$—4) is flash-chromatographed on neutral silica gel using a 98:2 by volume mixture of chloroform and methanol as eluent. Isomer A has a melting point of 113°–115° C. (ethyl acetate-hexane, 1:1 by volume). Anal. Calcd. for C$_{20}$H$_{23}$N$_3$O$_4$: C, 65.03; H, 6.28; N, 11.37. Found: C, 65.03; H, 6.28; N, 11.35. Isomer B has a melting point of 118°–120° C. (ethyl acetate-hexane, 1:1 by volume). Anal. Calcd. for C$_{20}$H$_{23}$N$_3$O$_4$: C, 65.03; H, 6.28; N, 11.37. Found: C, 64.73; H, 6.30; H, 11.22.

The compounds of the invention where R is phenyl or lower alkyl phenyl can be prepared according to the method of Example 1 by substituting for 4-chlorostyrene the styrenes,
styrene, bp 145°–146° C.
4-methylstyrene, bp 170°–175° C.,
and 3-methylstyrene, bp 170°–171° C.

The compounds of the invention where R is phenoxymethyl or lower alkylphenoxymethyl can be prepared according to the method of Example 3 by substituting for allyl 4-chlorophenyl ether the allyl ethers,
allyl phenyl ether, bp 192° C.
or allyl 4-methylphenyl ether, bp 97°–98° C.

Salts of the compounds of the invention can be prepared as known in the art, for example, by dissolving the compound in a 10:1 by volume mixture of ethanol and aqueous acid such as HCl or HNO$_3$, evaporating the solvent, and then recrystallizing the crude salt, for example, from methanol-ether, 1:3 by volume in the case of HCl salts, and ethanol in the case of HNO$_3$ salts.

We claim:

1. A compound of the formula:

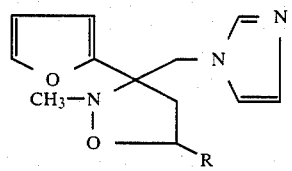

and the pharmaceutically acceptable acid addition salts thereof, in the form of their enantiomers or mixtures of their enantiomers including diastereoisomeric pairs of such enantiomers, wherein;
R is selected from phenyl, mono-, di- or tri-substituted phenyl and phenoxymethyl and mono-, di- or tri-substituted phenoxymethyl groups wherein the substituents on the substituted phenyl and phenylmethoxy groups are selected from halogen, nitro, lower alkyl, lower alkoxy and combinations thereof.

2. The compound of claim 1 wherein the compound is 5-(4-chlorophenyl)-3-(2-furanyl)-3-(1H-imidazol-1-ylmethyl)-2-methylisoxazolidine.

3. The compound of claim 1 wherein the compound is 3-(2-furanyl)-3-(1H-imidazol-1-ylmethyl)-2-methyl-5-(3-nitrophenyl)isoxazolidine.

4. The compound of claim 1 wherein the compound is 5-(4-chlorophenoxymethyl)-3-(2-furanyl)-3-(1H-imidazol-1-ylmethyl)-2-methylisoxazolidine.

5. The compound of claim 1 wherein the compound is 3-(2-furanyl)-3-(1H-imidazol-1-ylmethyl)-5-(4-methoxyphenoxymethyl)-2-methylisoxazolidine.

* * * * *